(12) United States Patent
Prescott

(10) Patent No.: US 9,155,545 B2
(45) Date of Patent: Oct. 13, 2015

(54) SURGICAL DRILL HANDPIECE WITH ADJUSTABLE CUTTING TOOL GUARD

(71) Applicant: Enteroptyx, Inc., Memphis, TN (US)

(72) Inventor: Anthony D. Prescott, Arlington, TN (US)

(73) Assignee: ENTEROPTYX, INC., Memphis, TN (US)

( * ) Notice: Subject to any disclaimer, the term of this patent is extended or adjusted under 35 U.S.C. 154(b) by 202 days.

(21) Appl. No.: 14/068,025

(22) Filed: Oct. 31, 2013

(65) Prior Publication Data

US 2015/0119889 A1   Apr. 30, 2015

(51) Int. Cl.
A61B 17/16   (2006.01)
B23B 49/00   (2006.01)

(52) U.S. Cl.
CPC ......... *A61B 17/1679* (2013.01); *A61B 17/1615* (2013.01); *A61B 17/1622* (2013.01); *A61B 17/1633* (2013.01); *A61B 17/162* (2013.01); *B23B 49/003* (2013.01)

(58) Field of Classification Search
CPC ............. A61B 17/162; A61B 17/1615; A61B 17/1633; B23B 49/003
See application file for complete search history.

(56) References Cited

U.S. PATENT DOCUMENTS

| | | | |
|---|---|---|---|
| 3,712,352 A | 1/1973 | Lafferty, Sr. | |
| 4,232,535 A | 11/1980 | Caldwell | |
| 4,486,176 A | 12/1984 | Tardieu et al. | |
| 4,568,642 A | 2/1986 | DeForrest et al. | |
| 4,705,038 A | 11/1987 | Sjostrom et al. | |
| 4,811,736 A | 3/1989 | Griggs et al. | |
| 4,964,839 A | 10/1990 | Gloor | |
| 4,995,877 A | 2/1991 | Ams et al. | |
| 5,263,218 A | 11/1993 | Giuliani et al. | |
| 5,405,348 A | 4/1995 | Anspach, Jr. et al. | |
| 5,569,967 A | 10/1996 | Rode | |
| 5,609,602 A | 3/1997 | Machemer et al. | |
| 5,796,188 A | 8/1998 | Bays | |
| 5,810,828 A | 9/1998 | Lightman et al. | |
| 6,047,456 A | 4/2000 | Yao et al. | |
| 6,126,670 A | 10/2000 | Walker et al. | |
| 6,425,761 B1 | 7/2002 | Eibofner | |
| 6,517,560 B1 | 2/2003 | Toth et al. | |
| 6,722,668 B2 | 4/2004 | Huggins et al. | |

(Continued)

FOREIGN PATENT DOCUMENTS

EP    1732452    7/2010

OTHER PUBLICATIONS

Otologic Drills and Burs, Revolutionary Design for Neurotology, Medtronic Inc., 2008.

*Primary Examiner* — Andrew Yang
(74) *Attorney, Agent, or Firm* — Gordon & Jacobson, PC

(57) ABSTRACT

A system includes a handpiece and a removable tool assembly including a holder body, a shaft, a cutting bur, a guard, and a sleeve. The body engages the handpiece and defines a bore. The shaft extends within the bore and the bur is provided to the distal end of the shaft. The guard is coupled to the body via a threaded mating at the bore, such that rotation of the guard relative to the body longitudinally displaces the guard. The extends within the bore of the body and the guard. The guard is positioned relative to the body by a distance to define a working length of the bur between the distal end of the guard and the distal tip of the bur. The working length of the bur is used to cut tissue, without concern that cutting will be deeper than intended.

20 Claims, 3 Drawing Sheets

(56) References Cited

U.S. PATENT DOCUMENTS

| | | |
|---|---|---|
| 6,887,244 B1 | 5/2005 | Walker et al. |
| 7,210,881 B2 | 5/2007 | Greenberg |
| 7,294,947 B2 | 11/2007 | Corbin, III et al. |
| 7,337,697 B2 | 3/2008 | Bader et al. |
| 7,771,143 B2 | 8/2010 | Bharadwaj et al. |
| 8,126,564 B2 | 2/2012 | Gantz |
| 8,403,916 B2 | 3/2013 | Prescott |
| 2010/0094306 A1 | 4/2010 | Chang et al. |
| 2011/0125176 A1 | 5/2011 | Yates et al. |

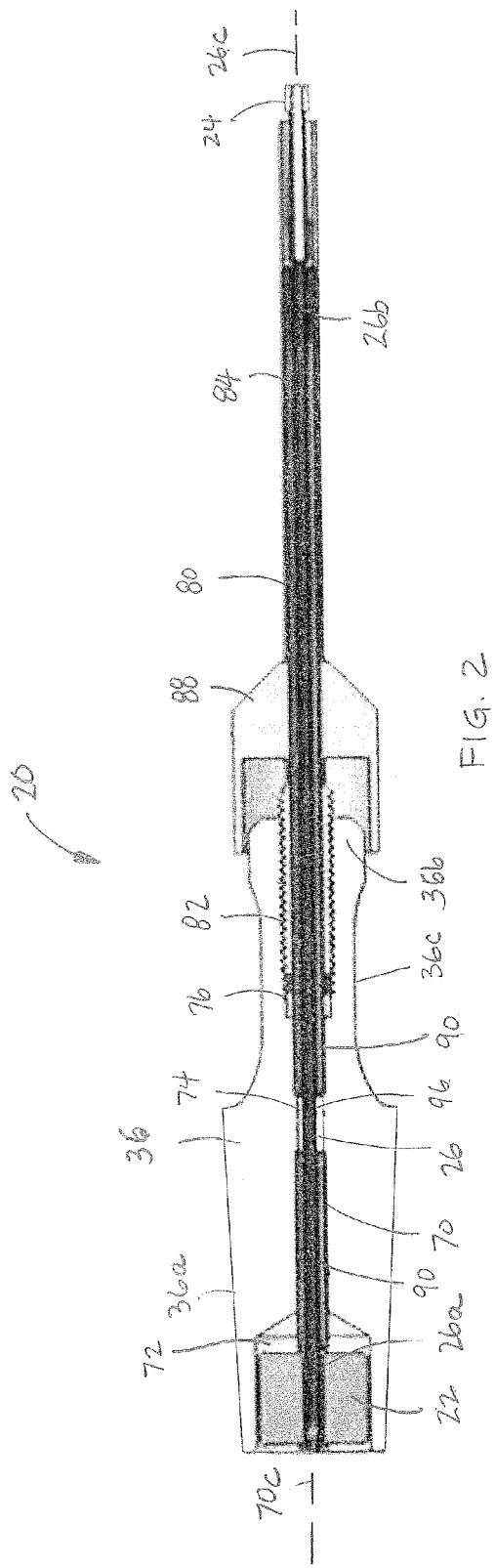
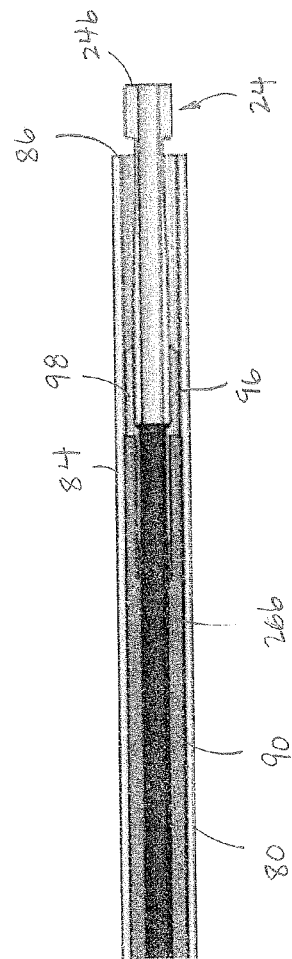
FIG. 2
FIG. 3

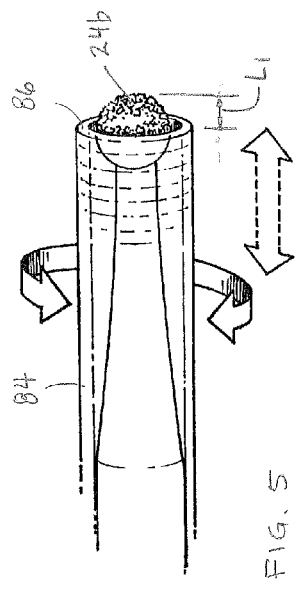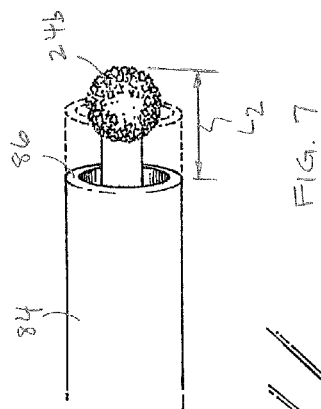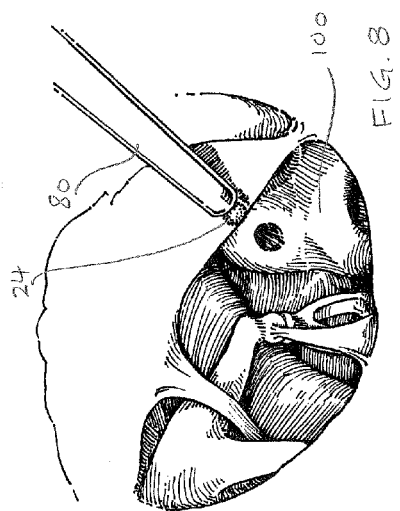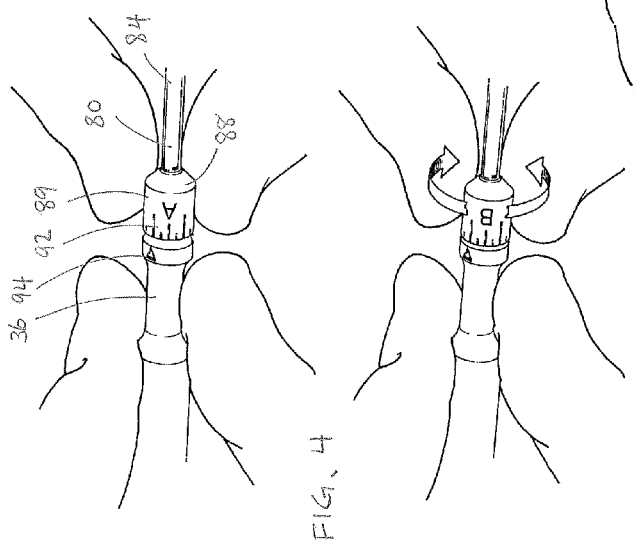

SURGICAL DRILL HANDPIECE WITH ADJUSTABLE CUTTING TOOL GUARD

CROSS-REFERENCE TO RELATED PATENT

This application is related to U.S. Pat. No. 8,403,916, which is hereby incorporated by reference herein in its entirety.

BACKGROUND OF THE INVENTION

1. Field of the Invention

The present invention relates to surgical instrumentation, and more particularly surgical drill handpieces. More specifically, the invention relates to handpieces for driving otology burs and guards therefor which are advantageously used during a cochleostomy and other surgical procedures in which it is desired to protect one anatomic structure by controlling the depth of a cutting instrument while removing another structure with the cutting instrument.

2. State of the Art

A cochlear implant is a hearing device that can be implanted in an individual with a severe or profound sensorineural hearing loss to directly stimulate the cochlear nerves and restore hearing. When successfully implanted, the cochlear implant restores a sufficient sense of sound, albeit with a different quality than natural sound, so that the recipient is able to hear and understand speech and environmental sounds. The performance of the cochlear implant is greater when there is some residual acoustic hearing capacity and a hearing aid is used in conjunction with the cochlear implant. See, for example, U.S. Pat. No. 8,126,564 to Gantz. In order to preserve the acoustic hearing, it is of vital importance that the membranous structures of the cochlea not be damaged during the surgical implant procedure.

The implant includes an external portion and an internal portion. The external portion is surgically placed under the skin behind the ear, and includes one or more microphones which picks up sound from the environment, a speech processor which selectively filters sound to prioritize audible speech, splits the sound into channels and sends the electrical sound signals through a thin cable to the transmitter, and a transmitter, which is a coil held in position by a magnet placed behind the external ear, and transmits power and the processed sound signals across the skin to the internal device by electromagnetic induction. The internal portion is secured in the cochlear bone beneath the skin, and includes a receiver and stimulator, which converts the signals into electric impulses and sends them through an internal cable to electrodes. The electrodes are wound through the cochlea, send the impulses to the nerves in the scala tympani and then directly to the brain through the auditory nerve system.

In order to pass the electrodes, a small hole must be drilled into the bony cochlea. A high-speed bur driving surgical handpiece is used to drill into the cochlea. However, it is a very delicate procedure, and extreme precision is required to ensure that the hole is drilled through the boney outer surface of the cochlea, but that no damage results to the interior cochlear membranes. The difficulty is rendered higher given that the depth of the boney surface is not consistent among patients. The surgeon must progressively remove bone from the cochlear wall while visually observing the color change at the bony surface to determine when the cochlear wall is about to be penetrated with the bur.

In such procedures, it is known to use a bur guard about the rotating shaft of the bur to protect peripherally surrounding tissue from the rapidly rotating shaft of the bur. However, such burs do not practically operate to limit the drilling depth of the bur.

SUMMARY OF THE INVENTION

A bur driver system according to the invention includes a high speed otologic driver handpiece, and a bur tool assembly driven by the handpiece. The bur tool assembly includes a tool holder body, a tool shaft, a cutting tool such as a bur, a bur guard, and bearing sleeve between the tool shaft and the bur guard. The tool holder body has a proximal portion which engages a socket provided to the handpiece, a distal end, and defines a longitudinal bore extending through the body. The tool shaft extends within the bore and is permanently retained relative to the holder body. The tool shaft has proximal structure by which the driver handpiece is adapted to apply a torque thereto to rotate the tool shaft about a tool shaft axis. The cutting bur is fixed or replaceable relative to the distal end of the tool shaft, with rotation of the tool shaft resulting in rotation of the cutting bur in a cutting motion. The tubular bur guard has a proximal end coupled to the holder body, preferably via a threaded mating at the bore of the holder body, such that rotation of the bur guard relative to the holder body longitudinally displaces the distal end of the bur guard relative to the holder body. The bearing sleeve is retained in the bore of the holder body and extends within the bur guard, and provides for stable and free rotation of the shaft.

The bur guard has an inner diameter and open distal end sized to permit advancement of the cutting bur therethrough. Displacement of the distal end of the bur guard relative to the holder body sets a defined working (cutting) length of the cutting bur extending beyond the distal end of the bur guard. The distal end of the bur guard functions as a stop to prevent cutting deeper than the set working length of the cutting bur, even though the cutting bur may have a significantly longer length extending within and protected by the bur guard.

In accord with preferred aspects of the invention, the bur guard includes a manual adjustment knob portion extending peripherally about the guard and adjacent a distal end of the holder body. The knob portion and distal end portion of the holder body are provided with respective indicia to indicate the working length of the cutting bur. Additionally, the knob provides greater purchase to effect rotation thereof relative to the holder body and effect change in the working length of the cutting bur.

In use, the bur guard is moved or otherwise set relative to the tool holder body so that the distal end of the bur guard is even with the distal tip of said cutting bur. Then, the bur guard is retracted relative to the tool holder body by a set distance to define an exposed length of the cutting bur between the distal end of the bur guard and the distal tip of the cutting bur. The exposed length of the cutting bur is then used to cut tissue, without concern that cutting will be deeper than intended. Particularly, the hard tissues of the ear, including the cochlea can be cut while protecting the delicate interior membranes.

BRIEF DESCRIPTION OF THE DRAWINGS

FIG. 2 is a longitudinal section view of the cutting tool assembly of the invention.

FIG. 3 is an enlarged distal end longitudinal section view of the cutting tool assembly of the invention.

FIG. 4 is a perspective view of a central portion of the cutting tool assembly held in hands of a user, particularly showing the proximal end of the guard in a first rotational and longitudinal position relative to the tool holder.

FIG. 5 is a perspective broken distal end view of the cutting tool assembly, illustrating the first position of the cutting tool relative to the distal end of the guard from the relative positions of the guard and tool holder in FIG. 4.

FIG. 6 is a view similar to FIG. 4, showing the proximal end of the guard in a second rotational and longitudinal position relative to the tool holder.

FIG. 7 is a perspective broken distal end view of the cutting tool assembly, illustrating the second position of the cutting tool relative to the distal end of the guard from the relative positions of the guard and tool holder shown in FIG. 6.

FIG. 8 illustrates use of the tool assembly to drill a hole of a predetermined depth in the cochlea of the inner ear.

DETAILED DESCRIPTION OF THE PREFERRED EMBODIMENTS

Figure 1:
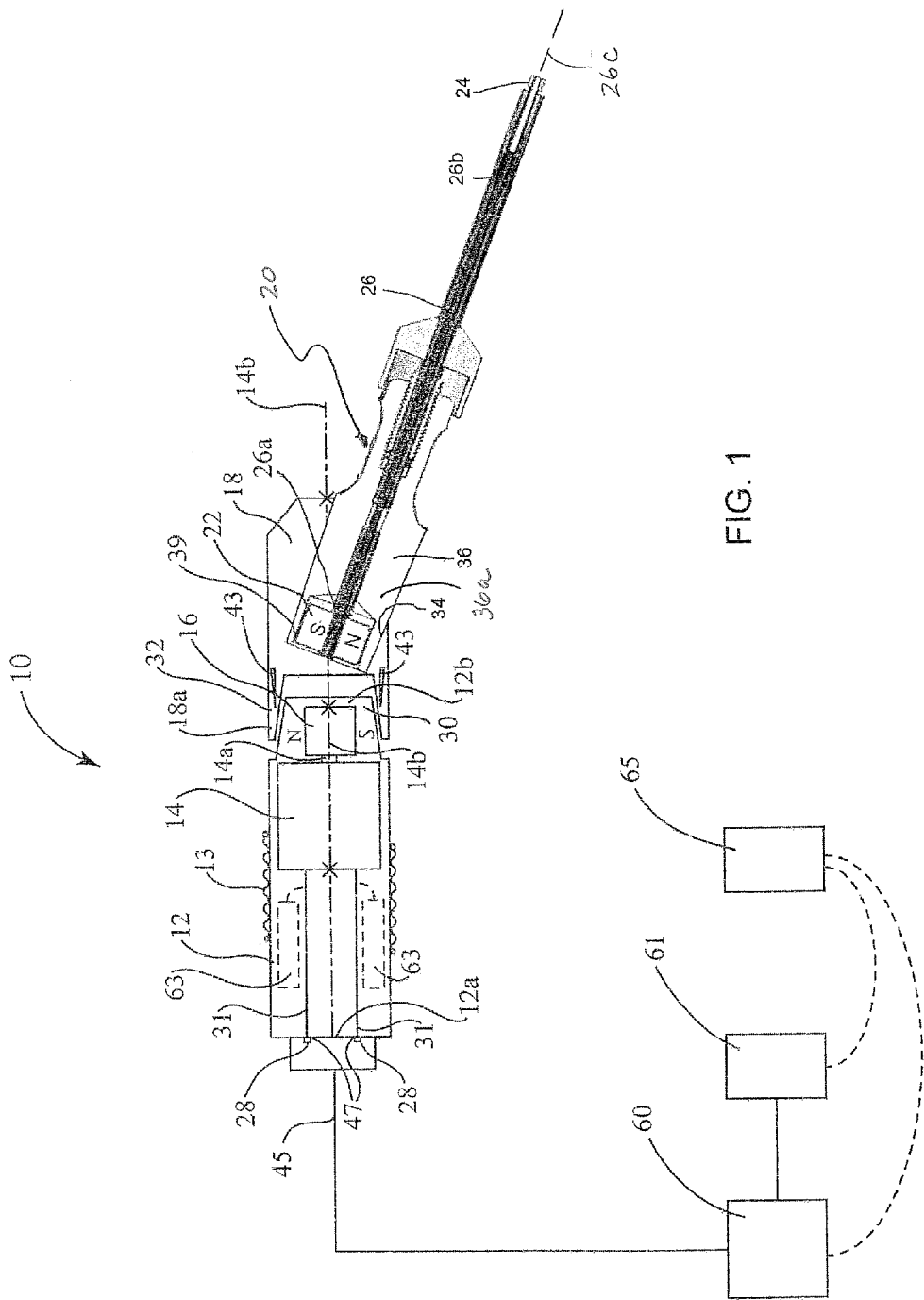
FIG. 1 is a longitudinal section view and part schematic view of the cutting tool driver system of the invention.

Referring to FIG. 1, a system according to an embodiment of the invention is shown. The system generally includes an otology drill handpiece 10, and a replaceable tool assembly 20 retained relative to the handpiece.

The handpiece 10 includes a housing 12, an electric motor 14 mounted within the housing 12, a drive magnet 16 coupled to and rotated by the motor 14, and a tool mount 18 preferably detachably coupled to the housing 12, but optionally fixed relative thereto. The replaceable tool assembly 20 is coupled to the handpiece at the tool mount 18.

More particularly, the housing 12 of the surgical instrument 10 preferably comprises an elongate, hollow, hermetically sealed metal or plastic structure which defines one or more hermetically sealed power connectors 28 at a proximal end 12a and a male taper portion 30 at a distal end 12b. The housing 12 is hermetically sealed to protect the motor 14 and drive magnet 16, particularly during sterilization. The housing 12 optionally includes a resilient sleeve 13 for gripping the instrument 10 and reducing any vibrations which may be caused by operation of the instrument 10.

The electric motor 14 includes a drive shaft 14a rotatable about a drive axis 14b. The drive shaft 14a and the drive magnet 16 fixed at its distal end are situated inside the male taper portion 30 at the distal end 12b of the housing 12. Wires 31 extending from the motor 14 connect to the power connectors 28 at the proximal end 12a of the housing 12. The power connectors 28 are attached to a power supply 60 via a power cable 45. Sealant 47 is applied at the edges of the power connectors 28 to hermetically seal the housing 12.

The drive magnet 16 is preferably cylindrically shaped and magnetized with opposite polarity (north and south) on opposite sides of its diameter as designated by the letters N and S in FIG. 1. The drive magnet 16 encircles the drive shaft 14a of the motor 14, and has a central axis which is co-axial with the drive axis 14b.

The tool mount 18 is preferably made from PEEK plastic and, in the illustrated embodiment, defines a female portion 32 at a proximal end 18a which mates with the male taper portion 30 of the housing 12 in a frictional taper lock. The taper lock may be similar to, for example, a leur lock. The tool mount 18 may also define one or more expansion slots 43 which allow the female portion 32 to expand slightly to accommodate the male taper portion 30 of the housing 12. The mount 18 is meant to be fairly rigidly coupled to the housing 12, and must be strong enough to withstand forces transmitted through the tool assembly 20. While the frictional locking of the male taper portion 30 and the female portion 32 is sufficient, rotation or other movement of the mount 18 may be further prevented with additional structure. Again, as an alternate construction, the tool mount 18 may be permanently integrated with the housing 12.

The mount 18 defines a female socket 34 for receiving and positioning the tool assembly 20 at a desired angle relative to the drive axis 14b of the motor 14. As described in more detail in previously incorporated U.S. Pat. No. 8,403,916, the angle of a central axis of through the socket 34 relative to the drive axis 14b may vary between 0° and 90°, and more preferably 0° and 45° depending on the desired angle of the tool assembly 20 relative to the drive axis 14b for access to a treatment site and comfort to the surgeon.

Referring to FIGS. 1 and 2, the replaceable tool assembly 20 includes a tool holder body 36, a tool shaft 26, a cutting tool in the form of a bur bit 24, a tubular cutting tool guard 80, and a bearing sleeve 90, all described in more detail below. The connection between the tool holder body 36 and the socket 34 of the tool mount 18 is preferably via an interference fit accommodated by the tapered fit of a proximal portion 36a of the tool holder body 36 within the socket 34 of the mount 18, or via another mechanical engagement. The mount 18 positions and retains the tool housing 36 of the tool assembly 20 such that the tool magnet 22 is in magnetic communication with the drive magnet 16. In this manner, rotation of the drive magnet 16 by the motor 14 causes movement of the tool magnet 22, and consequent movement of the tool shaft 26 and cutting bur 24. For purposes of a surgical procedure of interest, i.e., performing a cochleostomy, the cutting bur preferably has a diameter of less than 1 mm.

The tool holder body 36 of the tool assembly 20 includes the proximal portion 36a, a distal end 36b, a narrow waist 36c between the proximal portion and distal end 36a, 36b, and a longitudinal bore 70 extending longitudinally through the entire holder body 36. The narrow waist 36c facilitates manual gripping of the tool holder body 36 during removal and insertion of the tool assembly into the socket 34, and during adjustment of the tubular bur guard 80 relative to the tool holder body 35 as described in detail below. The longitudinal bore 70 has an enlarged proximal portion 72, a narrow central portion 74, and an enlarged distal threaded portion 76.

The bur guard 80 is preferably a monolithic tube; i.e., a one-piece metal tubular construct. The guard 80 is threadedly coupled to the holder body 36. The guard 80 includes an externally threaded proximal end 82 that mates with the threaded distal portion 76 of the longitudinal bore 70, a longitudinally extending tubular guard portion 84 extending therefrom and defining a distal end 86 of the guard 80, and a manual adjustment knob portion 88 extending peripherally about the guard 80 adjacent the distal end 36b of the holder body 36. Referring to FIG. 2 and FIGS. 4 through 7, rotation of the knob portion 88 relative to the holder body 36 causes the distal end 86 of the bur guard 80 to displace from over at least a portion of the tip 24b of the cutting bur 24 as the proximal end 82 of the guard 80 is thread into and out of the distal portion 76 of the bore. As the two elements are displaced, the exposed working length of the cutting bur extending from the distal end 86 of the guard 80 is altered (from $L_1$ to $L_2$), and a cutting depth of the bur is thereby defined; i.e., the cutting bur can cut no deeper than the length of which is exposed. More specifically, the distal end 86 of the bur guard 80 functions as a stop that will abut the bone, and that prevents cutting deeper than the defined cutting depth of the cutting bur 24. Thus, as described in more detail below, rotation of the knob portion 88 allows the surgeon to pre-set a selective penetration of the bur into the cochlea and prevents penetration beyond to the delicate interior membranes.

Referring to FIG. 4, the outer periphery 89 of the knob portion 88 is formed with indicia 92 (by way of example graduated marks, letters: (A, B, C, D), numbers, other symbols, or a combination of two or more thereof) that when referenced relative to a registration mark 94 on the holder body 36 can be used to indicate the exposed length of the cutting bur extending beyond the distal end of the bur guard 80. Referring to FIGS. 4 and 6, in one embodiment, a plurality of the indicia 92 (e.g., letters A, B, C, D) may be provided to indicate each 0.25 mm, or finer, of adjusted cutting depth, discussed further below. With reference back to FIG. 2, this can be accurately determined in relation to the thread pitch between the mated threaded portion 76 of the bore 70 and the threaded proximal end 82 of the bur guard 80. The thread pitch is preferably between 0.5 mm and 2.0 mm. As discussed in detail below, the exposed length of the bur can preferably be set within a range of 0.1 mm to 5.0 mm with an accuracy of at least 0.5 mm, and more preferably 0.025 mm; although other suitable operable ranges and accuracies can be identified and set. While the knob portion 88 is preferably unitary with the remainder of the tubular guard 80, as an alternative it may be a separate component rotationally fixed thereto.

Still referring to FIG. 2, the bearing sleeve 90 extends within the bore 70 and is longitudinally and preferably rotationally fixed relative to the bore 70, e.g., by interference engagement at a notch 96.

The rotatable tool shaft 26 extends through the bearing sleeve 94. The tool shaft 26 is securely supported by but rotatable within the bearing sleeve 94 about a tool shaft axis 26c coaxial with the bore axis 70c of the bore 70, and is preferably made from flexible spring steel wire or tubing with an outer diameter in the range of 0.020 to 0.028 inches. The diameter of the sleeve 94 is preferably small enough to contact the tool shaft 26 to prevent wobbling or lateral movement of the tool shaft 26, but not so small as to restrict rotation or longitudinal translation of the tool shaft 26 relative to the bearing sleeve 94. The proximal end 26a of the tool shaft 26 is coupled to a drive means for driving the shaft. In a preferred embodiment, the drive includes a drive magnet 22 (shown) for the magnetic drive system of the drill handpiece 10, or appropriate means for engagement with a pneumatic drive system, hydraulic drive system or a direct or reduction-gear electric drive system to provide for controlled high speed rotation of the tool shaft 26 and consequently the bur bit 24. The magnetic drive system with drive magnet 22 is described in more detail in previously incorporated U.S. Pat. No. 8,403,916. Referring to FIG. 3, the distal end 26b of the tool shaft 26 carries a bur holder 98 that receives the bur bit 24. The bur holder 98 may be permanently integrated with the bur bit 24 or may be adapted to permit an exchange of one bit for another, i.e., selective release and secure capture of a bit.

Preferably, the bur guard 80 is constructed of a plastically deformable metal such that the bur guard 80 and the bearing sleeve 90 may be manually bent along a curve by a surgeon or other user to retain such curved shape. If the guard 80 and sleeve 90 are bent by a user, then the portion of the shaft 26 inside of the guard 80 and sleeve 90 will simply bend with the guard 80 and sleeve 90. This allows the surgeon to facilitate an approach to the anatomy with the cutting bur while holding the handpiece at an angle offset from the rotational axis of the distal tip 24b of the cutting bur, as may be advantageous for sight lines to the surgical field or for physical clearance relative to anatomical structure. It is nevertheless recommended, rather than significantly bending the guard 80 and sleeve 90, that a user utilize an appropriate angle mount or angle adjustable mount designed to orient the tool assembly at the appropriate angle, as described in described in in previously incorporated U.S. Pat. No. 8,403,916. A user may then bend the guard and sleeve to make minor directional adjustments as needed.

In use, the bur guard 80 is moved or otherwise set relative to the tool holder body 36 so that the distal end 86 of the bur guard 80 is even with the distal tip 24b of the cutting bur 24. The position of the indicia 92 relative to the registration mark 94 is noted by the user. Then, the knob portion 88 of the bur guard 80 is rotated to retract the distal end 86 of the bur guard 80 relative to the distal tip 24b of the cutting bur. Specifically, the indicia 92 provide relative depth indicator marks in relation to the registration mark 94. That is, once the initial position of the indicia to the registration mark is known, and it is known how far the bur guard is retracted for the movement of each indicia past the registration mark, it can be determined the exact amount the bur guard has been retracted for a given degree of rotation for the knob relative to the tool holder body.

The following is provided by way of example only, and not by way of limitation. The mating thread between the bore 76 of the tool holder body and the bur proximal guard 82 has a thread pitch of 1 mm. The registration mark 94 is provided to the knob portion 88 of tool holder body 36, and four indicia (A, B, C, D) are evenly radially displaced about the circumference of the knob portion. Rotational movement of the knob portion relative to the tool holder body between each of the four labeled indicia, i.e., from each of A to B (as shown from FIGS. 4 to 6) and B to C and C to D and D back to A will indicate a retraction of 0.25 mm. For each full revolution of the knob portion relative to the tool holder body, the bur guard will be retracted the distance of the thread pitch, or in the exemplar case 1 mm. Where the distal end 86 of the bur guard is even with the distal tip 24b of the cutting bur (FIG. 7), the closest indicia is set as a zero mark. Once the zero mark is known; rotational adjustment of the knob to the registration mark is made in reference to this zero mark. Additional indicia can be provided for finer adjustment. Greater length adjustment can be effected by maintaining count of the number of the revolutions of the knob portion relative to the tool holder body.

The handpiece is then activated. Referring back to FIG. 1, the motor may be activated by push button, switch, foot pedal or other suitable means 61. For example, the foot pedal 61 could be depressed by a user to activate the motor 14 and or change the direction of rotation of the shaft 26 by the motor 14. The motor 14 is powered by an external power source 60 electrically coupled to the motor 14 via the wires 31. The motor 14 may alternatively be powered by batteries 63 (shown in phantom lines) situated within the housing 12. It is also contemplated that the instrument 10 could be activated and operated by wireless means 65 remotely coupled to the external power supply 60 and/or switch/foot pedal 61.

Activation of the motor 14 rotates the drive shaft 26 and drive magnet 16 about the drive axis 14b. Rotation of the drive magnet 16 about the drive axis 14b induces rotation of the tool magnet 22 attached to the drive shaft 26 on account of the magnetic coupling between the magnets (16, 22). The structure of the mount 18 and tool assembly 20 in conjunction with the forces applied to the tool magnet 22 via the magnetic coupling between the drive magnet 16 and the tool magnet 22 thus guide the movement of the cutting bur 24 in rotation about the tool shaft 26 along axis 26c.

Referring to FIG. 8, once the cutting bur 24 is rotating in high speed, it can be used to cut hard tissues, particularly at the inner ear, including the hard outer tissue of the cochlea 100. The distal end of the tool assembly is brought into contact with the cochlea, with the cutting bur 24 penetrating the hard outer tissue until the distal end of the bur guard contacts the tissue. At that time, the bur guard 80 functions as a stop to limit the depth of cutting, thereby protecting the delicate interior membranes of the cochlea. Moreover, even at the preset depth, the cutting bur may be used to cut laterally without interference from the bur guard, but with the bur guard maintaining its depth control function.

There have been described and illustrated herein embodiment of a drilling system, tool assembly, and a method of drilling that restricts drilling depth. While particular embodiments of the invention have been described, it is not intended that the invention be limited thereto, as it is intended that the invention be as broad in scope as the art will allow and that the specification be read likewise. Thus, while a particular threaded mating between the guard and the tool holder body has been disclosed, it will be appreciated that another relative coupling can be used as well, provided that such mating allows for either continuous or discrete longitudinal displacement of the guard relative to the holder body to allow setting of a working length of the cutting tool. Also, while a bur has been shown as an exemplar cutting tool, other cutting tools can similarly be provided to the distal end of the shaft, including hollow cutting tools. It will therefore be appreciated by those skilled in the art that yet other modifications could be made to the provided invention without deviating from its spirit and scope as claimed.

What is claimed is:

1. A tool assembly for use with a surgical drill handpiece having a socket for receiving the tool assembly, comprising:
   a) a tool holder body having a proximal portion with a proximal end, a distal portion with a distal end, and defining a longitudinal bore extending between said proximal and distal ends, said proximal portion adapted for engagement with the socket of the drill handpiece, and said bore having a threaded portion and defining a bore axis;
   b) a tool shaft having a proximal end and a distal end, said tool shaft extending within said bore and permanently retained relative to said tool holder body, and said tool shaft rotatable about a tool shaft axis, said proximal end of said tool shaft having structure by which said drill handpiece is adapted to apply a torque to said tool shaft to rotate said tool shaft about said tool shaft axis;
   c) a cutting tool coupled relative to said distal end of said tool shaft, such that rotation of said tool shaft results in rotation of said cutting tool, said cutting tool having a length;
   d) a tubular tool guard having a proximal end, a distal end and a central portion, said proximal end threadedly coupled related to said threaded portion of said bore, and said distal end having an opening sized to permit advancement of said cutting tool therethrough, said cutting tool freely rotatable relative to said tool guard, wherein rotation of said tool guard relative to said holder body longitudinally displaces said distal end of said tool guard relative to said holder body and sets of a defined working length of said length of said cutting tool extending beyond said distal end of said tool guard; and
   e) a bearing sleeve retained in said bore and extending within said tool guard, said shaft extending within and freely rotatable relative to said bearing sleeve,
      wherein said working length is adapted to be constant while said tool is retained in the socket of the drill handpiece and said handpiece applies the torque to said tool shaft.

2. A tool assembly according to claim 1, wherein:
one of said tool holder body and said tool guard includes a registration mark and the other of said tool holder body and said tool guard includes indicia, and referencing said indicia relative to said registration mark provides an indication of said working length of said cutting tool.

3. A tool assembly according to claim 2, wherein:
said tool guard includes a knob portion provided with said one of said registration mark and said indicia, said knob portion situated adjacent said tool holder body.

4. A tool assembly according to claim 1, wherein:
said tool guard is plastically deformable, and said shaft is rotatable relative to said bearing sleeve and said tool guard when said tool guard is plastically deformed.

5. A tool assembly according to claim 1, wherein:
said tool holder body includes a narrowed waist between its proximal and distal ends.

6. A tool assembly according to claim 1, wherein:
said proximal portion of said holder body is tapered for engagement with the socket of the handpiece.

7. A tool assembly according to claim 1, wherein:
said tool shaft is longitudinally fixed relative to said holder body.

8. A tool assembly according to claim 1, wherein:
said cutting tool is sized for cutting a hole not exceeding 1 mm in diameter.

9. A tool assembly according to claim 1, wherein:
said indicia is provided such that said working length can be adjusted in 0.25 mm increments.

10. A tool assembly according to claim 1, wherein:
said working length is adjustable in length between 0.1 mm and 5.0 mm.

11. A tool assembly according to claim 1, wherein:
said structure by which said drill handpiece is adapted to apply a torque is a magnet rotationally fixed relative to said proximal end of said shaft, said magnet having a magnet diameter, and said magnet magnetized with opposite polarity on opposite sides of said magnet diameter.

12. A tool assembly for use with a surgical drill handpiece having a socket for receiving the tool assembly, consisting essentially of:
   a) a tool holder body having a proximal portion with a proximal end, a distal portion with a distal end, and defining a longitudinal bore extending between said proximal and distal ends, said proximal portion adapted for engagement with the socket of the drill handpiece, and said bore having a threaded portion and defining a bore axis;
   b) a tool shaft having a proximal end and a distal end, said tool shaft extending within said bore and permanently retained relative to said tool holder body, and said tool shaft rotatable about a tool shaft axis, said proximal end of said tool shaft having structure by which said drill handpiece is adapted to apply a torque to said tool shaft to rotate said tool shaft about said tool shaft axis;
   c) a cutting tool coupled relative to said distal end of said tool shaft, such that rotation of said tool shaft results in rotation of said cutting tool, said cutting tool having a length;
   d) a tubular tool guard having a proximal end, a distal end and a central portion, said proximal end threadedly coupled related to said threaded portion of said bore, and said distal end having an opening sized to permit advancement of said cutting tool therethrough, said cutting tool freely rotatable relative to said tool guard, wherein rotation of said tool guard relative to said holder body longitudinally displaces said distal end of said tool guard relative to said holder body and sets of a defined working length of said length of said cutting tool extending beyond said distal end of said tool guard; and e) a bearing sleeve retained in said bore and extending within said tool guard, said shaft extending within and freely rotatable relative to said bearing sleeve.

13. A surgical drilling system, comprising:
a) a surgical drill handpiece, including,
   a housing,
   a socket provided to said housing,
   a motor mounted to said housing, said motor having a drive shaft rotatable about a drive shaft axis, and
   a drive system coupled to said drive shaft; and
b) at least one replaceable tool assembly detachably coupled within said socket, said tool assembly including,
   i) a tool holder body having a proximal end, a distal end, and defining a longitudinal bore extending between said proximal and distal ends, said bore having a threaded portion and a bore axis,
   ii) a tool shaft having a proximal end and a distal end, said tool shaft extending within said bore and permanently retained relative to said holder body, said tool shaft rotatable about a tool shaft axis, said proximal end of said tool shaft having structure which operably couples relative to said drive shaft such that rotation of said drive shaft about said drive shaft axis results in rotation of said tool shaft about said tool shaft axis,
   iii) a cutting tool coupled relative to said distal end of said tool shaft, such that rotation of said tool shaft results in rotation of said cutting tool, said cutting tool having a length,
   iv) a tubular tool guard having a proximal end, a distal end and a central portion, said proximal end threadedly coupled related to said threaded portion of said bore, and said distal end having an opening sized to permit advancement of said cutting tool therethrough, said cutting tool freely rotatable relative to said tool guard, wherein rotation of said tool guard relative to said holder body longitudinally displaces said distal end of said tool guard relative to said holder body and sets of a defined working length of said length of said cutting tool extending beyond said distal end of said tool guard, and
   v) a bearing sleeve retained in said bore and extending within said tool guard, said shaft extending within and freely rotatable relative to said bearing sleeve.

14. A method of drilling with a surgical handpiece, comprising:
a) providing a surgical drilling system including,
   i) a surgical drill handpiece, and
   ii) at least one replaceable tool assembly detachably coupled relative to said handpiece, said tool assembly including, A) a tool holder body having a proximal end, a distal end, and defining a longitudinal bore extending between said proximal and distal ends, B) a tool shaft having a proximal end and a distal end, said tool shaft extending within said bore rotatable about a tool shaft axis, said tool shaft rotated by operation of said drill handpiece, C) a cutting tool coupled relative to said distal end of said tool shaft such that rotation of said tool shaft results in rotation of said cutting tool, said cutting tool having a length and a distal tip, and D) a tubular tool guard having a proximal end and a distal end, said distal end having an opening sized to permit advancement of said cutting tool therethrough, said cutting tool freely rotatable relative to said tool guard, wherein said tool guard may be longitudinally displaced at a set location relative to said tool holder body to define an exposed working length of said length of said cutting tool extending beyond said distal end of said tool guard;

b) moving the tool guard relative to said tool holder body so that said distal end of said tool guard is even with said distal tip of said cutting tool;

c) retracting said tool guard relative to said holder body by a set distance to define an exposed working length of said cutting tool between said distal end of said tool guard and said distal tip of said cutting tool; and d) cutting into a hard tissue with said working length of said cutting tool.

15. A method according to claim 14, wherein:
said tool guard and said tool holder body are coupled relative to each other by a threaded mating, and wherein said moving and said retracting are carried out by rotation of tool guard relative to said tool holder body.

16. A method according to claim 15, wherein:
one of said tool holder body and said tool guard includes a registration mark and the other of said tool holder body and said tool guard includes indicia, and referencing said indicia relative to said registration mark provides an indication of said exposed length of said cutting tool.

17. A method according to claim 15, wherein:
said threaded mating includes a thread pitch of 0.5 mm to 2.0 mm.

18. A method according to claim 14, wherein:
said hard tissue is inner ear tissue.

19. A method according to claim 18, wherein:
said inner ear tissue is a cochlea.

20. A method according to claim 14, wherein:
said cutting includes pressing said cutting tool into said hard tissue until said distal end of said tool guard contacts said hard tissue.

* * * * *